United States Patent [19]
Beden et al.

[11] Patent Number: 5,836,908
[45] Date of Patent: Nov. 17, 1998

[54] DISPOSABLE BALANCING UNIT FOR BALANCING FLUIDS, AND RELATED MEDICAL TREATMENT DEVICE

[75] Inventors: Josef Beden, Mainz-Kastel; Hans-Jurgen Flaig, Lauterbach; Bernd Steinbach, Friedberg, all of Germany

[73] Assignee: Fresenius Aktiengesellschaft, Bad Homburg, Germany

[21] Appl. No.: 762,084

[22] Filed: Dec. 9, 1996

[30] Foreign Application Priority Data

Dec. 9, 1995 [DE] Germany ............ 195 46 028.6

[51] Int. Cl.⁶ ........................... A61M 1/28
[52] U.S. Cl. ............... 604/29; 210/321.6; 210/321.64
[58] Field of Search ............... 604/4, 5, 29, 403, 604/405, 406, 408, 410; 210/646, 321.3, 321.4, 321.8, 321.6, 321.64; 206/419, 420

[56] References Cited

U.S. PATENT DOCUMENTS 3,709,222  1/1973  DeVries .
4,366,061  12/1982  Papanek et al. .

FOREIGN PATENT DOCUMENTS 34 28 828  4/1989  Germany .
41 16 178  11/1992  Germany .
WO 90/13795  11/1990  WIPO .

*Primary Examiner*—John G. Weiss
*Assistant Examiner*—David J. Cho
*Attorney, Agent, or Firm*—Kenyon & Kenyon

[57] ABSTRACT

A disposable balancing unit designed as a sheet bag includes two sheets (1, 2), which are heat-sealed together, forming a balancing chamber (4) that is divided by a flexible wall (8) into the two chamber halves (9, 10), and forming two equalization chambers (5, 6), as well as the channels (15 through 18) connecting the individual chambers. The flexible wall (8), which separates the first chamber half (9) of the balancing chamber (4) from the second chamber half (10), is formed by an intermediate sheet, which is inserted between the first and second sheet (1, 2) in the area of the balancing volume and is heat-sealed in a pressure-tight manner to the outer sheets, forming the first and second chamber half (9, 10). The fixed volume of the balancing chamber halves (9, 10) is specified by a corresponding system insert unit, into which the disposable unit is fittingly inserted. The system insert unit has two rigid receiving bodies (25, 26) with trough-shaped depressions (27) to grasp above or below the balancing chamber (4) of the disposable unit. The disposable balancing unit can be manufactured cost-effectively in a single heat-sealing operation and is easy to handle.

20 Claims, 3 Drawing Sheets

DISPOSABLE BALANCING UNIT FOR BALANCING FLUIDS, AND RELATED MEDICAL TREATMENT DEVICE

BACKGROUND OF THE INVENTION

1. Field of the Invention

The invention relates to a disposable balancing unit for balancing fluids for a medical treatment device, as well as to a medical treatment device having a system insert unit for accommodating such a disposable balancing unit.

2. Description of Related Art

When faced with chronic renal failure, different blood-purification or blood-treatment methods are applied, in which apparatuses are employed to remove those substances, which are usually eliminated with the urine, and to withdraw fluids. The predominant method used in hemodialysis (HD) is the diffusive transfer of substances; in hemofiltration (HF), it is the convective transfer of substances across a membrane. A combination of the two methods is called hemodiafiltration (HDF). In peritoneal dialysis (PD), no extracorporeal circuit is needed, and the peritoneum is used as the contact membrane.

Because of the large exchange volumes entailed in the named methods, as well as in continuous arteriovenous HF, continuous veno-venous HF, and in plasma-filtration (PF), there must be a precise balancing of the withdrawn fluid, on the one hand, and of the supplied fluid, on the other hand, and of the volume to be ultrafiltrated over the entire treatment time. Gravimetric and volumetric balancing systems are known from the related art.

The German Patent 41 16 178 C1 describes a device for purifying blood, in which a volumetric fluid balancing is performed for HF, HDF, and PF systems. The known hemotherapeutic device has a balancing chamber, which is partitioned by a flexible wall into a first and a second balancing-chamber half, the first chamber half communicating with a filtrate line, and the second chamber half with a substituate line. A filtrate outlet line branches off from the first chamber half to an outlet, while a substituate line, which communicates with the circulatory system, branches off from the second chamber half. The filtrate and the substituate are alternately supplied, as the case may be, to the balancing chamber from an equalization chamber which communicates with the filtrate or substituate line by means of a pressure device. When working with the known filtration device, the equalization chambers are filled by the filtrate pump or the substituate pump and, after the cut-off clamps are opened, are emptied by means of the pressure device into one of the balancing chamber halves, at the same time, the other balancing chamber half being emptied under the effect of pressure into the respective other outlet line. The balancing chamber and the equalization chambers make up a multipart set, which is discarded after a single use. The equalization chambers of the set are conceived as flexible plastic bags which communicate with the filtrate or substituate lines, while the housing of the balancing chamber is a rigid plastic body. Because the disposable unit of the known filtration device is made up of a multiplicity of individual components, its handling is difficult. In addition, it is relatively costly to manufacture the multipart disposable unit.

German Patent 34 28 828 C2 describes a device for conveying blood in an extracorporeal circuit, including a pump chamber, whose pump space has a continuous membrane that encloses a cavity. Disposed in the cavity is a reversing membrane, which is made of elastic material and has a hose shape that is joined at one of its ends to a connecting piece for two lines. The pump space of the pump chamber communicates via a line with a mechanical piston pump, enabling the pump space to be filled with a working fluid in order to compress the hose-shaped reversing membrane.

SUMMARY OF THE INVENTION

It is an object of the invention to provide a balancing disposable unit for balancing fluids for a medical treatment device, which will be easy to handle and inexpensive to manufacture. It is a further object of the invention to provide a medical treatment device with a system insert unit for accommodating a disposable balancing unit of this type.

The disposable balancing unit in accordance with the invention is designed as a sheet bag [film-type pouch] and, thus, has both a balancing chamber as well as two equalization chambers which are in fluid communication with the respective chamber halves of the balancing chamber. The disposable balancing unit is essentially comprised of two sheets, which are joined together in a pressure-tight manner, while forming the balancing chamber that is divided by a flexible wall into the two chamber halves, the two equalization chambers, as well as the channels connecting the individual chambers.

When working with the disposable balancing unit in accordance with the invention, the functional principle of volumetric balancing can be retained, whereby the two balancing chamber halves are alternately filled and emptied. The fixed volume of the balancing chamber halves is specified by a corresponding system insert unit, into which the disposable unit in accordance with the invention can be fittingly inserted. The system insert unit has two rigid receiving bodies with trough-shaped depressions to grasp above and below the balancing chamber of the disposable unit. When one of the two chamber halves is filled, the outer sheets of the disposable unit come up [place themselves] against the inner surfaces of the two shell-shaped halves, so that a specific balancing volume is defined. Also integrated in the system insert unit are known compression devices, which pressurize the equalization chambers that communicate with the first or second inlet channel. In addition, the channels are alternately clamped off using clamping devices, which are likewise installed in the system insert unit.

When the disposable balancing unit is used in the PD, the principle applies accordingly. In this case, however, substituate is not continuously balanced with the filtrate, but rather, using additional clamps and connections, fresh dialysate is first supplied via both balancing chamber halves and, after being retained in the abdominal cavity, the consumed dialysate is conveyed in the same manner into the outflow (bodily discharge), i.e., there is no direct displacement of substituate through the filtrate, and vice versa. The volumes [quantities] are balanced by adding the individual volumes which are carried away [removed] or supplied per chamber filling.

The disposable unit in accordance with the invention is able to be produced cost-favorably in a single heatsealing or bonding process. Since the disposable unit includes all components of the balancing device, its handling is substantially simplified. The one-piece disposable unit can be inserted with one flick of the wrist into the corresponding system insert unit of the medical treatment device, i.e., after use, it can be replaced with a new sheet bag. A very flat type of construction also proves to be advantageous, as it permits the flexible sheet bag to be offered as a sterile unit in a flat plastic pocket, which is insensitive to shock and can be stacked and transported very easily.

As a general principle, the sheets of the disposable balancing unit can be heat-sealed or bonded together. However, the sheets are preferably heat-sealed together to achieve a pressure-tight connection.

The flexible wall, which separates the first chamber half of the balancing chamber from the second chamber half, is formed by an intermediate sheet, which is inserted between the first and second sheets in the area of the balancing volume and is joined, e.g., heat-sealed or bonded, in a pressure tight manner with the outer sheet while forming the first and second chamber halves. Through proper heat-sealing in the inlets and outlets, and by placing the sheets under a pressure above atmosphere, two balancing chamber halves are created, which are completely separated by the intermediate sheet. When one chamber is filled, the same liquid volume is automatically pressed out into the other chamber.

Since material residues are formed at the edges of the seam when the sheet is heat-sealed, a relatively large contact pressure is required to clamp off the inlet and outlet channels in a pressure-tight manner. Therefore, flexible plastic hoses are advantageously inserted, at least in the area of the clamping spots of the channels, between the top and bottom sheet of the disposable unit, and are heat-sealed or bonded to the outer sheets. The channels, which are seamless on the inside, are able to be clamped off in a simple manner using relatively little pressure. Furthermore, the danger of the heat-sealed sheet channels collapsing when subjected to just a slight partial vacuum and interrupting the return flow is diminished by the flexible plastic hoses. The channels are advantageously clamped off using tappets, which are provided in the one receiving body of the system insert unit and which interact with clamping edges that are arranged on the opposite side in the other receiving body.

The disposable balancing unit is preferably provided with slots for receiving alignment pins, which can be integrated in the system insert unit. This ensures an exact positioning of the disposable unit between the receiving bodies of the system insert unit. The disposable unit is preferably retained at its edges within the system insert unit. Therefore, clamping edges, which grip the disposable unit from both sides, are advantageously provided in the receiving bodies of the system insert unit.

In one advantageous specific embodiment, a serpentine channel, which leads into the second equalization chamber, is formed in the disposable unit. The serpentine channel enables the fluid, which is directed into the second equalization chamber, to be tempered through the sheets using heating plates that are applied externally to the disposable unit. The heating plates can be conceived as a component of the receiving bodies of the system insert unit, the flow guidance and vorticity within the sheet being able to be ensured by a suitable structure in the insert unit.

In another preferred specific embodiment, the disposable balancing unit has a buffer chamber, which communicates with the second outlet channel. This buffer chamber makes it possible to convert the pulsating flow that occurs when only one balancing volume is used into a quasi continuous flow. The buffer effect is achieved, in this case, by means of mechanical coupling provided in the system insert unit, said mechanical coupling interacting with the disposable balancing unit and emptying the buffer chamber when the first equalization chamber is filled. By this means, the pressure monitoring on the blood side is simplified and needle pulsation is reduced.

The equalization chamber, which is preferably oval in shape for an improved lateral utilization, and the rectangular equalization chambers are preferably arranged with the longitudinal axis of the equalization chamber running transversely to the longitudinal axes of the equalization chambers. As a result, a space-saving chamber configuration is achieved.

The following will describe in detail two specific embodiments of the disposable balancing unit in accordance with the invention and one specific embodiment of the system insert unit of a hemotherapeutic device for receiving the disposable unit.

DETAILED DESCRIPTION OF THE INVENTION

Figure 1:
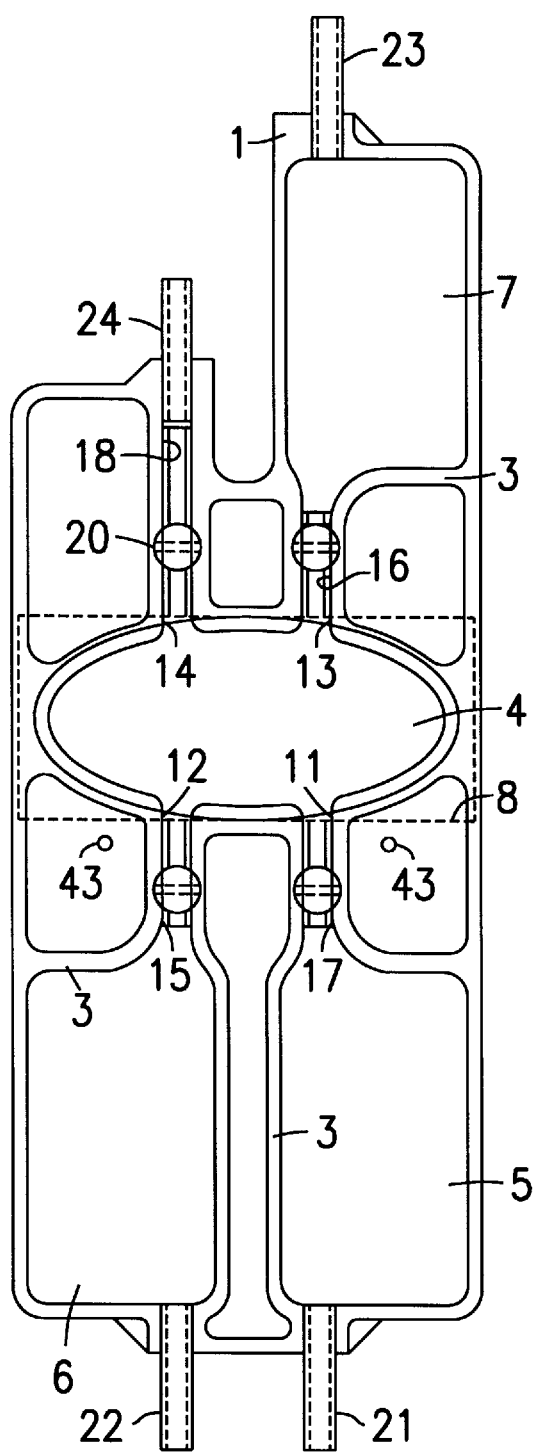
FIG. 1 is a plan view of the disposable balancing unit in accordance with the invention.

FIG. 1 shows the disposable balancing unit for a medical treatment device according to the invention. The disposable balancing unit has two flexible, essentially rectangular plastic sheets 1, 2, which are heat-sealed together along the seam positions denoted by reference numeral 3 so as to form altogether four chambers between the upper and lower sheets 1, 2. A balancing chamber 4 having an oval shape is situated in the center of the disposable unit. Arranged on one side of the balancing chamber are a first rectangular equalization chamber 5 and a second rectangular equalization chamber 6, which have the same intake volume. Disposed on the other side of balancing chamber 4 is a buffer chamber 7.

Balancing chamber 4 has a flexible and elastic wall 8, which divides the chamber into a first bottom and a second top chamber half 9, 10, each chamber half 9, 10 being provided with one inlet 11, 12 and one outlet 13, 14. As indicated by a dashed line in FIG. 1, flexible wall 8 is comprised of a rectangular intermediate sheet, which is inserted in the area of the balancing volume between the top and bottom sheet 1, 2, and is heat-sealed to the outer sheets 1, 2, while forming the two chamber halves 9, 10 (see FIG. 2).

The bottom chamber half 9 is connected in fluid communication via a first inlet channel 17 to the first equalization chamber 5, while the upper balancing chamber half is in fluid communication via a second inlet channel 15 with the second equalization chamber 6 and, via a diagonally opposed second outlet channel 16, with buffer chamber 7. A first outlet channel 18 is connected to outlet 14 of the first balancing chamber half 9. The inlet and outlet channels 15 through 18 are formed between chambers 4 through 7 by flexible plastic hoses 19, which are inserted between upper and lower sheets 1, 2, and are heat-sealed to the outer sheets. The inlets or the outlets of hoses 19 are so heat-sealed to intermediate sheet 8 of balancing chamber 4, that one inlet and one outlet are situated above, and one inlet and one outlet below intermediate sheet 8, and a direct connection is not given between the upper and lower balancing chamber halves 9, 10.

The inserted plastic hoses 19 not only prevent the hose channels from collapsing under a partial vacuum, but also create clamping spots 20, shown as circles in FIG. 1, which can be clamped off in a pressure-tight manner. Heat-sealed to the inlet of the first equalization chamber 5 is a first supply line 21, to the inlet of the second equalization chamber 6, a second supply line 22, to the end of the first outlet channel 18, a first outlet line 24, and to the outlet of buffer chamber 7, a second outlet line 23. Inlet and outlet lines 21 through 24 can be provided with connecting pieces (not shown in FIG. 1). In addition, to the side of the balancing chamber, the disposable balancing unit has slots 43 for receiving alignment pins. The chambers are to be understood here as bag arrangements.

The disposable balancing unit in accordance with the invention, can be used, for example, in a hemotherapeutic device which performs volumetric fluid balancing and has a filter that is divided by a semipermeable membrane into a blood chamber and a filtrate chamber. An extra-corporeal hemotherapeutic device of this type is known, for example, from German Patent 41 16 178 C1. If the disposable balancing unit is used in a hemo-therapeutic device of this type, the first equalization chamber 5 forms the filtrate-equalization chamber, and the second equalization chamber 6 the substituate-equalization chamber, while the first and second inlet channels 17, 15 form the filtrate- and substituate-inlet channels, and the first and second outlet channels 18, 16, the filtrate- and substituate-outlet channels. However, the disposable balancing unit in accordance with the invention can also be used advantageously in a peritoneal dialysis device, used for cyclically supplying peritoneal dialyzing fluid to and withdrawing it from a patient in an exactly balanced manner. For this purpose, the two supply lines 21, 22 are united to form one common inlet line, and the two outlet lines 23, 24 to form one common outlet line, the dialyzing fluid being directed via the common inlet line, alternately into first and second balancing chamber halves 9, 10, and via the common outlet line to the patient's peritoneal cavity. In a peritoneal dialyzer of this type, one buffer chamber advantageously communicates with the first outlet channel, and one buffer chamber with the second outlet channel. Alternatively, however, one buffer chamber can also be connected into the shared outlet line, following the junction point [the point where the lines are united].

Figure 2:
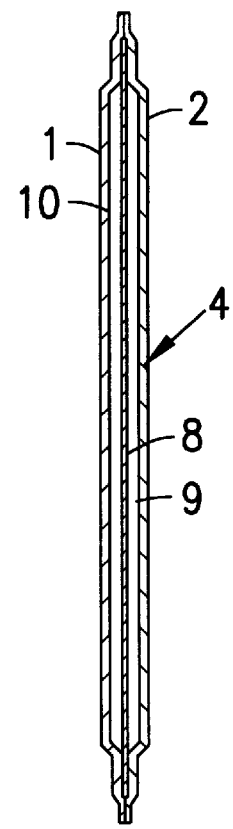
FIG. 2 is a sectional view through the balancing chamber of the disposable balancing unit.

FIG. 2 shows a section through balancing chamber 4 of the disposable balancing unit which is not filled with fluid. Intermediate sheet 8 is heat-sealed by its outer edge to the edges of the top and bottom sheet 1, 2 and is freely movable in balancing chamber 4 between the outer sheets. Since the elasticity of the plastic sheets makes it impossible for a constant volume to be observed, the balancing volume is defined by a fixed outer form. Therefore, the disposable balancing unit is inserted into a system insert unit, which is a component of the hemotherapeutic device. The system insert unit, which will be described in detail later on with reference to FIG. 5, has two receiving bodies 25, 26, each with a depression 27 provided in the area of the balancing volume.

Figure 3A:
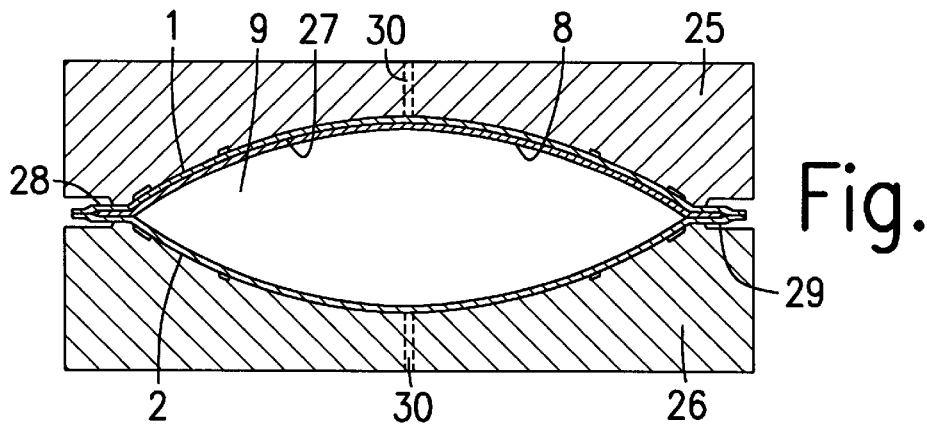
FIG. 3a is a sectional view through the balancing chamber of the disposable balancing unit situated between the two receiving bodies of the system insert unit, the bottom chamber half being filled and the upper chamber half being emptied.
Figure 3B:
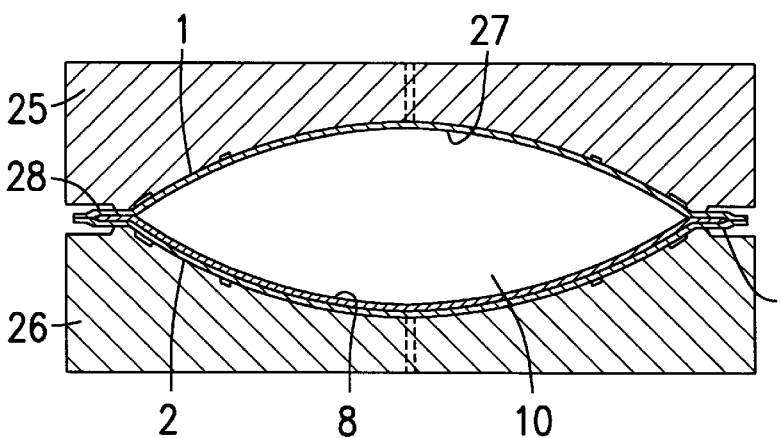
FIG. 3b is a sectional view through the balancing chamber of the disposable balancing unit situated between the two receiving bodies of the system insert unit, the bottom chamber half being emptied and the upper chamber half being filled.

FIGS. 3a and 3b show a section through the disposable unit's balancing chamber 4, which is situated between the two receiving bodies 25, 26 of the system insert unit. The upper and lower receiving bodies 25, 26 of the system insert unit are provided with a longitudinally running clamping edge 28, 29, which fixes the edge areas of the disposable balancing unit in position. If the volume situated between upper sheet 1 and intermediate sheet 8 is filled with fluid, then, when the inlets and outlets of balancing chamber 4 are opened and closed accordingly, the other volume between intermediate sheet 8 and bottom sheet 2 is emptied as a result of the displacement caused by the folding over of intermediate sheet 8 (FIG. 3b). For the top and bottom sheet 1, 2 of the disposable unit to be able to place themselves tightly against the shell shapes of receiving bodies 25, 26, vents 30 are provided in the receiving bodies.

Figure 4:
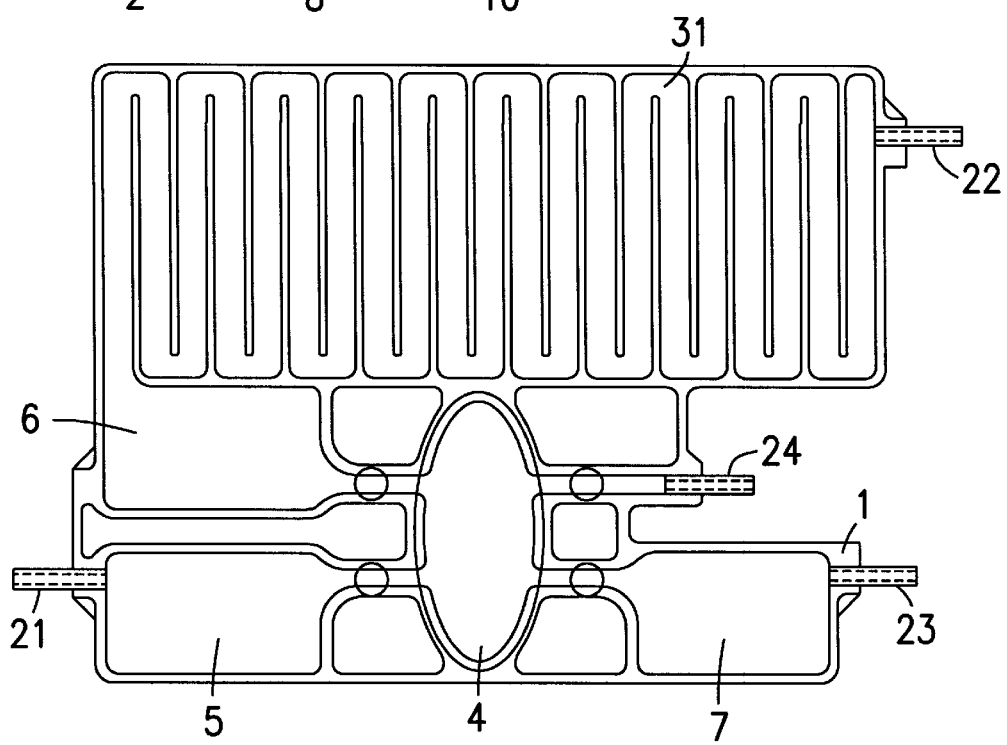
FIG. 4 illustrates a second specific embodiment of the disposable balancing unit having an integrated heating sheet.

FIG. 4 shows a second specific embodiment of the disposable balancing unit. The disposable balancing unit shown in FIG. 5 differs from the disposable unit described with reference to FIGS. 1 through 3 in that a serpentine channel 31 is formed, which leads into the second equalization chamber 6 and makes it possible for the supplied fluid to be tempered. The fluid is heated through the heating sheets by means of heating plates, which are provided in a corresponding system insert unit and are brought into contact with the heating sheet of the disposable unit. Temperature sensors (not shown in FIG. 4), capable of measuring the temperature at the surfaces of the two outer sheets 1, 2 in a simple manner, may be provided for regulating and temperature-monitoring purposes. At least one regulating and one protective sensor are expediently arranged downstream from the heating sheet. In addition, it may also be advantageous to have one other temperature sensor at the heating sheet inlet.

Figure 5:
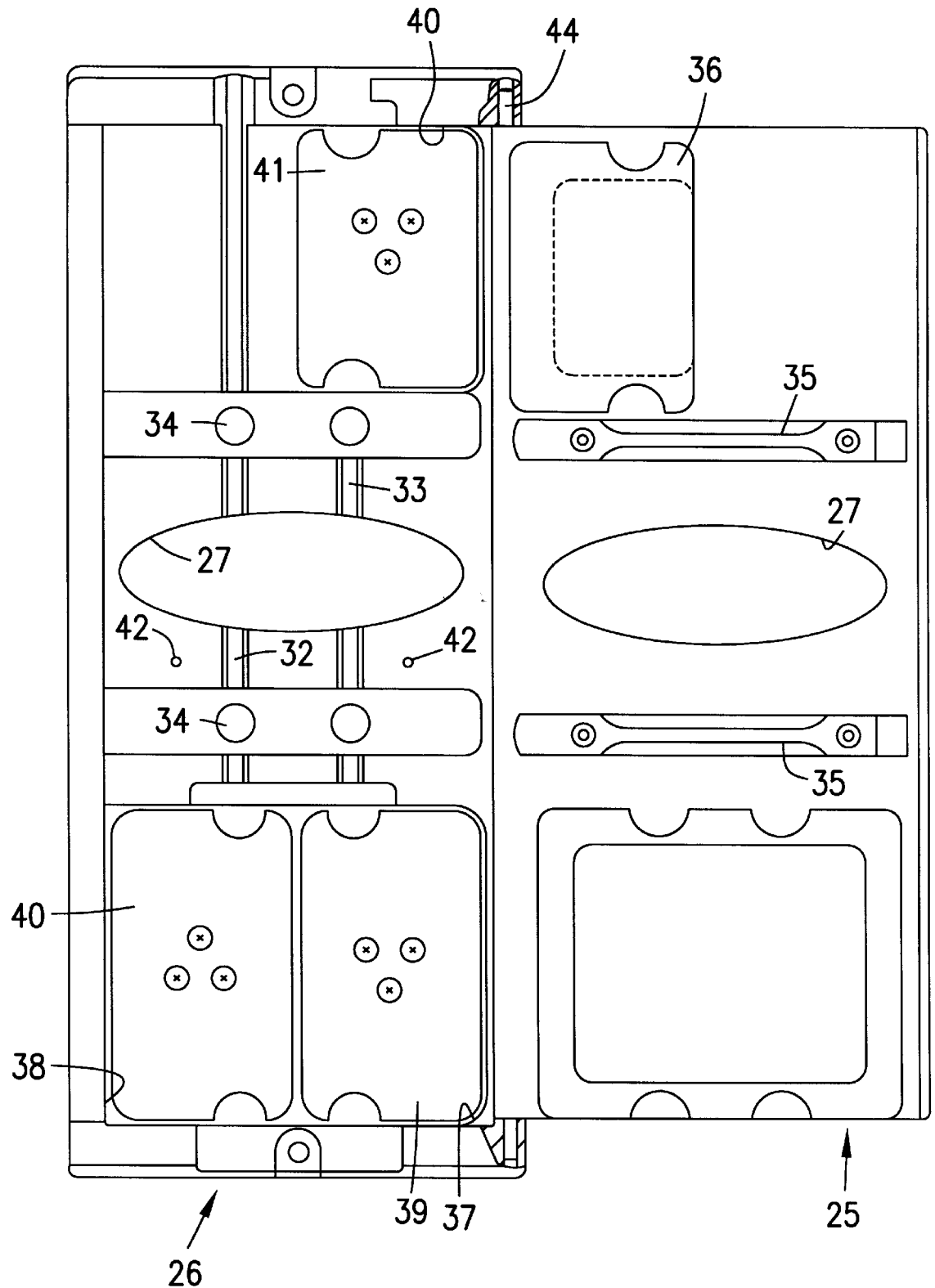
FIG. 5 illustrates the opened [unfolded] system insert unit of the medical treatment device with the two receiving bodies for accommodating the disposable balancing unit in accordance with the invention.
Figure 2:
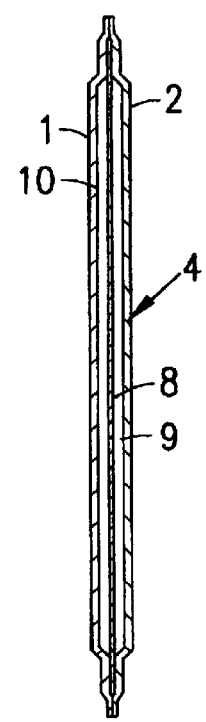

FIG. 5 shows a plan view of the opened [unfolded] system insert unit of the medical treatment device, into which the disposable balancing unit is fittingly inserted. The upper and lower receiving bodies 25, 26 of the system insert unit, whose external dimensions correspond to the disposable unit, are interconnected at their longitudinal sides by a hinge 44. Depressions 27 for receiving balancing chamber halves 9, 10 are arranged in the center of the two receiving bodies 25, 26. The disposable units are fixed in position using alignment pins 42, which engage in corresponding slots 43 of the disposable unit. Provided on both sides of depressions 27 in the lower receiving body 26 are two parallel guide channels 32, 33 for accommodating inlet and outlet channels 15–18. Also arranged within guide channels 32, 33 are four tappets 34, which interact with clamping edges 35 situated at the level of tappets 34 in the upper receiving body 25. Clamping spots 20 of the channels of the disposable unit can be clamped off in a pressure-tight manner using electromagnetically actuated tappets 34. Provided laterally next to tappets 34 or clamping edges 35 are insertion pieces 36, 37, 38 in the lower and upper receiving body 25, 26 for accommodating the first or second equalization chambers 5, 6, as well as buffer chamber 7. Arranged at the base of insertion pieces 37, 38 for the equalization chambers are the spring-prestressed pressure plates 39, 40 of the compression devices situated in the system insert unit, these compression devices being used to pressurize equalization chambers 5, 6 of the disposable unit. The functioning of the clamping devices and of the compression devices is described in German Patent 41 16 178 C1. Provided at the base of insertion piece 40 for buffer chamber 7 is an additional pressure plate 41. This pressure plate 41 can be so mechanically coupled to pressure plate 39 of the first equalization chamber that it executes an oppositely directed movement.

What is claimed is:

1. A disposable balancing unit for balancing fluids for a medical treatment device comprising: first and second superposed plastic sheets, which are joined together in a pressure-resistant manner, forming a balancing chamber in the unit that is divided by a flexible wall into a first and a second chamber half, said flexible wall of said balancing chamber being formed by an intermediate sheet, which is inserted between the first and second sheet in the area of the balancing volume and is so joined to the first and second sheets, forming the two chamber halves so that said first chamber half is separated in a pressure-tight manner from said second chamber half;

a first equalization chamber in the unit, which is in fluid communication with the first chamber half via a first inlet channel and, which is able to be clamped off in a pressure-tight manner;

a second equalization chamber in the unit, which is in fluid communication with the second chamber half via a second inlet channel, which is able to be clamped off in a pressure-tight manner; and a first outlet channel, which is able to be clamped off in a pressure-tight manner and is in fluid communication with said first chamber half, and a second outlet channel, which is able to be clamped off in a pressure-tight manner and is in fluid communication with said second chamber half.

2. The disposable balancing unit as defined by claim 1, wherein the inlet and outlet channels are formed at least in the area of the clamping spots by flexible plastic hoses, which are arranged between the first and second sheets and are joined in a pressure-tight manner to the first and second sheets.

3. The disposable balancing unit as defined by claim 2, wherein the first sheet, second sheet and intermediate sheet are in the same plane.

4. The disposable balancing unit as defined by claim 1, wherein the disposable balancing unit defines slots for receiving alignment pins.

5. The disposable balancing unit as defined by claim 2, wherein the disposable balancing unit defines slots for receiving alignment pins.

6. The disposable balancing unit as defined by claim 1, wherein the first and second sheets are joined together in a pressure-tight manner and form a serpentine channel which leads into the second equalization chamber.

7. The disposable balancing unit as defined by claim 2, wherein the first and second sheets are joined together in a pressure-tight manner and form a serpentine channel which leads into the second equalization chamber.

8. The disposable balancing unit as defined by claim 4, wherein the first and second sheets are joined together in a pressure-tight manner and form a serpentine channel which leads into the second equalization chamber.

9. The disposable balancing unit as defined by claim 5, wherein the first and second sheets are joined together in a pressure-tight manner and form a serpentine channel which leads into the second equalization chamber.

10. The disposable balancing unit as defined by claim 1, wherein the first and second sheets are joined together in a pressure-tight manner and form a buffer chamber which communicates with the second outlet channel.

11. The disposable balancing unit as defined by claim 2, wherein the first and second sheets are joined together in a pressure-tight manner and form a buffer chamber which communicates with the second outlet channel.

12. The disposable balancing unit as defined by claim 4, wherein the first and second sheets are joined together in a pressure-tight manner and form a buffer chamber which communicates with the second outlet channel.

13. The disposable balancing unit as defined by claim 6, wherein the first and second sheets are joined together in a pressure-tight manner and form a buffer chamber which communicates with the second outlet channel.

14. The disposable balancing unit as defined by claim 1, wherein the balancing chamber has an oval shape and the equalization chambers have a rectangular shape, said equalization chambers and said balancing chamber being so arranged that longitudinal axes of the equalization chambers run transversely to a longitudinal axis of the balancing chambers.

15. The disposable balancing unit as defined by claim 2, wherein the balancing chamber has an oval shape and the equalization chambers have a rectangular shape, said equalization chambers and said balancing chamber being so arranged that longitudinal axes of the equalization chambers run transversely to a longitudinal axis of the balancing chambers.

16. The disposable balancing unit as defined by claim 4, wherein the balancing chamber has an oval shape and the equalization chambers have a rectangular shape, said equalization chambers and said balancing chamber being so arranged that longitudinal axes of the equalization chambers run transversely to a longitudinal axis of the balancing chambers.

17. A medical treatment device for removing toxic substances from the blood, comprising a system insert unit for receiving the disposable balancing unit as defined by claim 1, the system insert unit having two rigid receiving bodies, which are provided with a trough-shaped depression and are situated in the area of the balancing chamber of the balancing disposable unit, and compression devices for pressurizing the equalization chambers of the disposable unit, and clamping devices for clamping off the inlet and outlet channels.

18. The medical treatment device as defined by claim 17, wherein the receiving bodies each have a clamping edge for fixing the edge areas of the sheet-type disposable unit in position.

19. The medical treatment device as defined by claim 17, wherein in one receiving body of the receiving bodies, the clamping devices are provided with tappets and, in an other receiving body of the receiving bodies, with clamping edges opposing said tappets.

20. The medical treatment device as defined by claim 18, wherein in one receiving body of the receiving bodies, the clamping devices are provided with tappets and, in an other receiving body of the receiving bodies, with clamping edges opposing said tappets.

\* \* \* \* \*

(12) EX PARTE REEXAMINATION CERTIFICATE (8496th)
United States Patent
Beden et al.

(10) Number: US 5,836,908 C1
(45) Certificate Issued: Aug. 30, 2011

(54) DISPOSABLE BALANCING UNIT FOR BALANCING FLUIDS FOR A MEDICAL TREATMENT DEVICE HAVING A SYSTEM INSERT UNIT FOR ACCOMMODATING SUCH A DISPOSABLE BALANCING UNIT

(75) Inventors: Josef Beden, Mainz-Kastel (DE); Hans-Jurgen Flaig, Lauterbach (DE); Bernd Steinbach, Friedberg (DE)

(73) Assignee: Fresenius AG, Bad Homburg, V.D.H. (DE)

Reexamination Request:
No. 90/010,241, Nov. 13, 2008

Reexamination Certificate for:
Patent No.: 5,836,908
Issued: Nov. 17, 1998
Appl. No.: 08/762,084
Filed: Dec. 9, 1996

(51) Int. Cl.
*A61M 01/28* (2006.01)

(52) U.S. Cl. ............. 604/29; 210/321.6; 210/321.64
(58) Field of Classification Search ............ None
See application file for complete search history.

(56) References Cited

U.S. PATENT DOCUMENTS

| | | |
|---|---|---|
| 3,054,401 A | 9/1962 | Gewecke |
| 3,709,222 A | 1/1973 | DeVries |
| 3,774,762 A | 11/1973 | Lichtenstein |
| 4,167,663 A | 9/1979 | Granzow |
| 4,209,391 A | 6/1980 | Lipps et al. |

FOREIGN PATENT DOCUMENTS

DE 41 16 178 C 1 11/1992

OTHER PUBLICATIONS

English translation of Beden–DE 41 16 178 C 1.*

* cited by examiner

*Primary Examiner*—Glenn K. Dawson

(57) ABSTRACT

A disposable balancing unit designed as a sheet bag includes two sheets (1, 2), which are heat-sealed together, forming a balancing chamber (4) that is divided by a flexible wall (8) into the two chamber halves (9, 10), and forming two equalization chambers (5, 6), as well as the channels (15 through 18) connecting the individual chambers. The flexible wall (8), which separates the first chamber half (9) of the balancing chamber (4) from the second chamber half (10), is formed by an intermediate sheet, which is inserted between the first and second sheet (1, 2) in the area of the balancing volume and is heat-sealed in a pressure-tight manner to the outer sheets, forming the first and second chamber half (9, 10). The fixed volume of the balancing chamber halves (9, 10) is specified by a corresponding system insert unit, into which the disposable unit is fittingly inserted. The system insert unit has two rigid receiving bodies (25, 26) with trough-shaped depressions (27) to grasp above or below the balancing chamber (4) of the disposable unit. The disposable balancing unit can be manufactured cost-effectively in a single heat-sealing operation and is easy to handle.

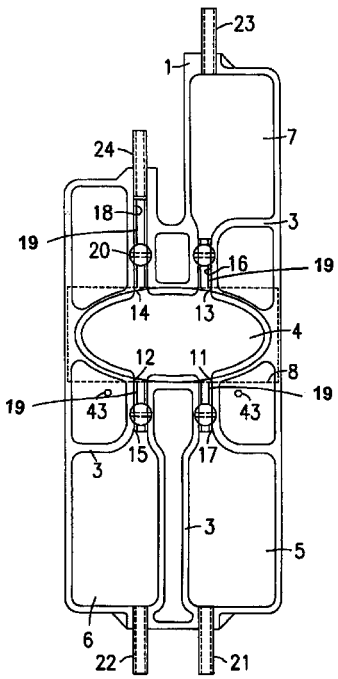

Amended

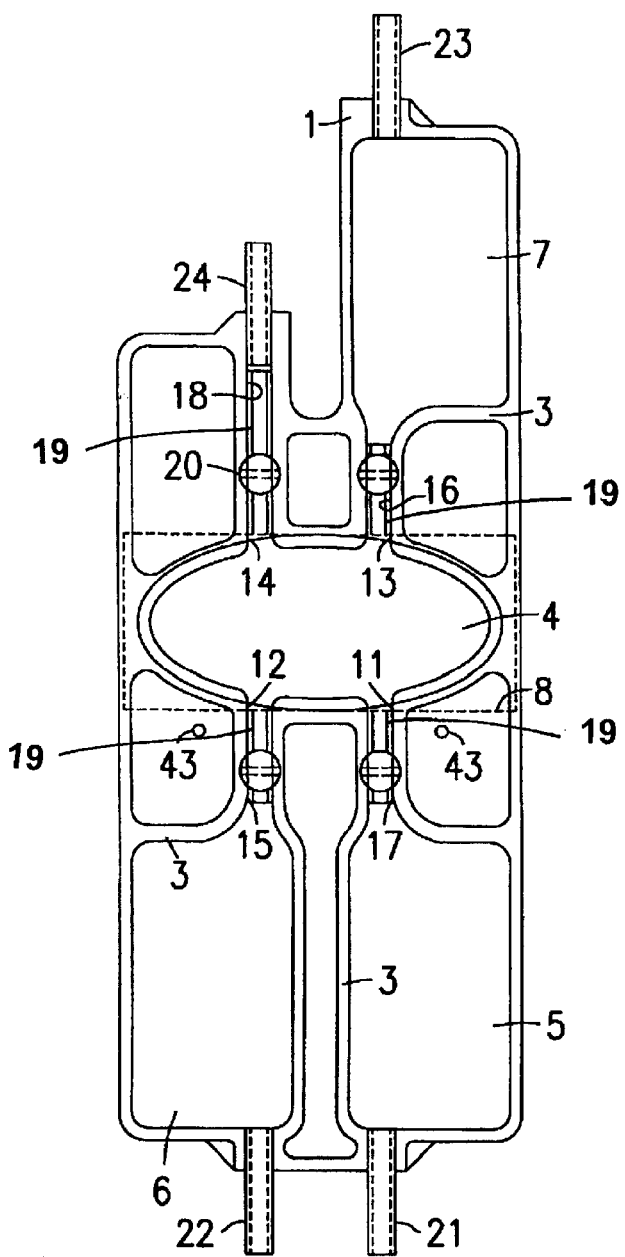
Fig. 1
Amended

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 7-19:

The flexible wall, which separates the first chamber half of the balancing chamber from the second chamber half, is formed by an intermediate sheet, which is inserted between the first and second sheets in the area of the balancing volume and is joined, e.g., heat-sealed or bonded, in a pressure tight manner with the outer sheet while forming the first and second chamber halves. Through proper heat-sealing in the inlets and outlets, and by placing the sheets under a pressure above [atmosphere] *atmospheric pressure*, two balancing chamber halves are created, which are completed separated by the intermediate sheet. When one chamber is filled, the same liquid volume is automatically pressed out into the other chamber.

Column 6, lines 21-38:

FIG. 4 shows a second specific embodiment of the disposable balancing unit. The disposable balancing unit shown in FIG. [5] *4* differs from the disposable unit described with reference to FIGS. 1 through 3 in that a serpentine channel 31 is formed, which leads into the second equalization chamber 6 and makes it possible for the supplied fluid to be tempered. The fluid is heated through the heating sheets by means of heating plates, which are provided in a corresponding system insert unit and are brought into contact with the heating sheet of the disposable unit. Temperature sensors (not shown in FIG. 4), capable of measuring the temperature at the surfaces of the two outer sheets 1, 2 in a simple manner, may be provided for regulating and temperature-monitoring purposes. At least one regulating and one protective sensor are expediently arranged downstream from the heating sheet. In addition, it may also be advantageous to have one other temperature sensor at the heating sheet inlet.

THE DRAWING FIGURES HAVE BEEN CHANGED AS FOLLOWS:

FIG. 1, add reference numeral 19.

AS A RESULT OF REEXAMINATION IT HAS BEEN DETERMINED THAT:

The patentability of claims 19 and 20 is confirmed.

Claims 1-18 are cancelled.

New claim 21 is added and determined to be patentable.

*21. The disposable balancing unit as defined by claim 17, further comprising vents in the receiving bodies.*

\* \* \* \* \*